United States Patent [19]

Kobayashi et al.

[11] Patent Number: 5,072,027

[45] Date of Patent: Dec. 10, 1991

[54] PROCESS FOR PRODUCING METHACRYLIC ACID ESTERS

[75] Inventors: Akihiro Kobayashi; Toshio Akima, both of Ichihara; Takayuki Saito; Toshiyuki Fujita, both of Hitachi, all of Japan

[73] Assignee: Hitachi Chemical Company, Ltd., Tokyo, Japan

[21] Appl. No.: 416,993

[22] Filed: Oct. 4, 1989

[30] Foreign Application Priority Data

Oct. 6, 1988 [JP] Japan .................. 63-252634
Oct. 6, 1988 [JP] Japan .................. 63-252635
Oct. 6, 1988 [JP] Japan .................. 63-252637

[51] Int. Cl.$^5$ .............................................. C07C 67/02
[52] U.S. Cl. .................................................... 560/217
[58] Field of Search ........................................ 560/217

[56] References Cited

U.S. PATENT DOCUMENTS 4,791,221 12/1988 Gabillet ............................. 560/217
4,916,255 4/1990 Kobayashi ......................... 560/217

FOREIGN PATENT DOCUMENTS 0210907 2/1987 European Pat. Off. .
2744641 4/1979 Fed. Rep. of Germany .
1094998 12/1967 United Kingdom .

*Primary Examiner*—Paul J. Killos
*Attorney, Agent, or Firm*—Antonelli, Terry, Stout & Kraus

[57] ABSTRACT

In a process for producing a methacrylic acid ester by subjecting methyl methacrylate and an alcohol to a transesterification reaction in the presence of a catalyst and a polymerization inhibitor, the filtration time of catalyst and the like can be shortened by making a total water content in the catalyst, alcohol and methyl methacrylate 1000 ppm or less, or the generation of large bubbles during the reaction can be prevented by adding the starting alcohol to the reaction system at the alcohol conversion of 40% or more, or high catalytic activity is obtained even if a secondary or tertiary alcohol is used as a starting material by using as a catalyst that obtained by drying lithium hydroxide monohydrate with heating, these effects being also obtained by combining individual conditions.

18 Claims, No Drawings

PROCESS FOR PRODUCING METHACRYLIC ACID ESTERS

BACKGROUND OF THE INVENTION

This invention relates to a process for producing a methacrylic acid ester.

One problem in the production of methacrylic acid esters is that a time required for filtration for removing a catalyst and the like is long.

For example, Japanese Patent Unexamined Publication No. 54-61117 proposes a process for producing a methacrylic acid ester by a transesterification reaction using lithium hydroxide as a catalyst, but the time for requiring filtration for removing the catalyst and the like is long. This seems to be caused by the fact that most of the catalyst lithium hydroxide is converted to a lithium salt of methacrylic acid, which is a very fine powder and causes clogging of the filter to prolong the filtration time.

Another problem in the production of methacrylic acid esters is that large bubbles are generated in a reactor during the reaction to cause a flooding phenomenon in a rectifying column by the bubbles, resulting in making the operation difficult.

As is well known in the art, a methacrylic acid ester is produced by a process wherein methyl methacrylate and an alcohol are subjected to a transesterification reaction in the presence of a transesterification catalyst and a polymerization inhibitor. The transesterification reaction of methyl methacrylate and an alcohol is an equilibrium reaction and can be usually proceeded by removing produced methanol by azeotropic distillation with methyl methacrylate. Further, in order to enhance the reaction rate and suppress the production of polymers, it is general to use methyl methacrylate in an excess amount with regard to the alcohol, and to remove the methyl methacrylate by distillation after the transesterification reaction, followed by a purifying step such as filtration, distillation, and the like. For this reason, a batch type operation is usually employed for the production of methacrylic acid esters. Further, the transesterification reaction is generally carried out by using a tank type reactor equipped with a stirrer and a rectifying column for azeotropic distillation of methyl methacrylate and methanol.

In order to carry out the transesterification reaction with industrially and economically high productivity, it is necessary to maintain an evaporating amount of methanol from the reactor more than the prescribed amount in order to reduce the methanol content in the reactor. Further, in order to prevent the loss of methyl methacrylate by distillation, it is necessary to properly control a reflux ratio at the rectifying column so as to make the mixture of methyl methacrylate and methanol to be distilled from the rectifying column near the azeotropic composition (methanol content 92% by mole) depending on the methanol concentration in the reactor.

The present inventors carried out the transesterification reaction for the production of methacrylic acid esters under proper evaporation amounts and reflux ratio as mentioned above, but large bubbles generated in the reactor to cause a flooding phenomenon in the rectifying column by the bubbles, resulting in making the operation difficult. In order to conduct the reaction smoothly, it was necessary to add methyl methacrylate and the alcohol in a volume of 45 to 60% of the capacity of the reactor, which resulted in reducing the yield and remarkably damaging the productivity.

A still further problem in the production of methacrylic acid esters is that when a secondary or tertially alcohol is used as a starting material, catalytic activity is lowered and separation of the catalyst by filtration is not easy.

Various catalysts have been studied in processes for producing methacrylic acid esters by a transesterification reaction of methyl methacrylate and an alcohol.

For example, it is proposed to use an acidic catalyst such as sulfuric acid or p-toluenesulfonic acid (Japanese Patent Examined Publication Nos. 48-21929 and 48-37011). But since the acidic catalyst is remarkably small in the activity, a long period of time is necessary for the reaction, and there easily takes place side reactions such as intramolecular dehydration reaction, and the like.

On the other hand, as a basic catalyst, an alkali metal alkoxide such as sodium methoxide is generally used (British Patent No. 976,304). This catalyst has defects in that the catalytic activity is lowered during the reaction and there easily takes place a side reaction of addition of the starting alcohol or by-produced alcohols to double bonds of the starting ester and the desired product.

It is also known a process wherein a titanium alkoxide is used as a catalyst having high selectivity for the reaction (U.S. Pat. No. 3,686,268). But since the titanium alkoxide loses its activity even if a very small amount of water is present in the reaction system, it is necessary to remove the water from the reaction system previously. Further, there is a defect in that in order to separate the titanium alkoxide from the reaction mixture after the reaction, it is necessary to conduct a treatment with, for example, a sodium hydroxide aqueous solution so as to produce an inert product by hydrolysis. Further, the titanium alkoxide sometimes does not substantially show a catalytic activity for dihydric or higher polyhydric alcohols. Thus, it is not a general synthetic catalyst for methacrylic acid esters and is limited undesirably for its use.

Apart from the above-mentioned processes, it is proposed to use lithium hydroxide as a catalyst (Japanese Patent Unexamined Publication No. 54-61117). Since lithium hydroxide is relatively excellent in the activity and selectivity and has a good catalytic activity for polyhydric alcohols, it is considered to be a suitable catalyst. But according to the experiments conducted by the present inventors using lithium hydroxide monohydrate, it was found that it was possible to remove the catalyst by filtration after the reaction, but there was a defect in that it took a remarkably long filtering time due to poor filtering properties. Further, when the transesterification reaction was carried out by using a secondary or tertially alcohol as a starting material, there was a defect in that the reaction hardly proceeded due to a remarkably low catalytic activity.

On the other hand, Japanese Patent Unexamined Publication No. 54-61117 discloses that lithium hydroxide can be used in the form of either containing water or not containing water. Industrially available one is lithium hydroxide monohydrate, and this reference does not describe concretely how to dehydrate the lithium hydroxide monohydrate. According to known methods [Kagaku Binran (Handbook of Chemistry), Application edition, the Chemical Society of Japan, 1980, published by Maruzen, Ltd.], anhydrous lithium hydroxide can be obtained by (1) gradually heating lithium hydroxide monohydrate on a silver boat at 140° C. in a hydrogen stream, or (2) drying lithium hydroxide monohydrate on phosphorus pentaoxide in vacuum for several days. Since these methods are complicated, require dangerous operations and can give only a very small amount of the anhydride at one time, it is very difficult to industrially use the anhydrous lithium hydroxide obtained by such methods.

SUMMARY OF THE INVENTION

It is an object of the present invention to provide a process for producing a methacrylic acid ester overcoming the above-mentioned problems.

The present inventors have further studied so as not to form the lithium salt of methacrylic acid in order to shorten the filtration time and found that the water content in the reaction system had a close relation to the yield of lithium salt of methacrylic acid, and attained the present invention.

The present invention provides a process for producing a methacrylic acid ester, which comprises subjecting an alcohol and methyl methacrylate to a transesterification reaction in the presence of a catalyst and a polymerization inhibitor, a total water content in the catalyst, alcohol and methyl methacrylate being 1000 ppm or less.

It is another object of the present invention to prevent generation of large bubbles in the reactor, to increase an yield per batch and to improve the productivity while maintaining a reaction rate and a composition distilled from a rectifying column in the production of a methacrylic acid ester.

The present invention also provides a process for producing a methacrylic acid ester, which comprises subjecting methyl methacrylate and an alcohol to a transesterification reaction in the presence of a transesterification catalyst and a polymerization inhibitor, while adding the same alcohol used as a starting material to the reaction system at a stage when the alcohol initially added becomes a conversion of 40% or more, or a later stage thereafter.

It is a further object of the present invention to provide a process for producing a methacrylic acid ester by a transesterification of reaction of methyl methacrylate and an alcohol in the presence of a catalyst which shows a high activity for not only primary alcohols but also secondary and tertiary alcohols and can easily be separated by filtration from the reaction mixture after the reaction. Further, said catalyst can be obtained by treating a compound which can easily be obtained industrially with an industrially easy method.

The present invention further provides a process for producing a methacrylic acid ester, which comprises subjecting an alcohol and methyl methacrylate to a transesterification reaction in the presence of a catalyst and a polymerization inhibitor, said catalyst being obtained by drying lithium hydroxide monohydrate with heating.

DESCRIPTION OF THE PREFERRED EMBODIMENTS

Esterification by transesterification reaction in the production of methacrylic acid esters is disclosed, for example, in Japanese Patent Unexamined Publication No. 54-61117, wherein an alcohol is reacted with methyl methacrylate in the presence of a catalyst and a polymerization inhibitor and produced methanol is removed from the system.

In the present invention wherein an alcohol and methyl methacrylate are subjected of the transesterification reaction in the presence of a catalyst such as lithium hydroxide and a polymerization inhibitor, while controlling a total water content in the catalyst, alcohol and methyl methacrylate at 1000 ppm or less, the following conditions are employed.

As the alcohol, there can be used, for example, tricyclo$[5.2.1.0^{2,6}]$decenol, tricyclo$[5.2.1.0^{2,6}]$decanol, tricyclo$[5.2.1.0^{2,6}]$decenoloxyethanol, tricyclo$[5.2.1.0^{2,6}]$decanyloxyethanol, tricyclo$[5.2.1.0^{2,6}]$decenyloxypropanol, tricyclo$[5.2.1.0^{2,6}]$decanyloxypropanol, tricyclo$[5.2.1.0^{2,6}]$decanyloxyethanol, tricyclo$[5.2.1.0^{2,6}]$decanyloxyethanol, cyclohexanol, cyclooctanol, cyclododencanol, borneol, phenetol, cyclopentanol, ethyl alcohol, propyl alcohol, butyl alcohol, penty alcohol, hexyl alcohol, 2-ethylhexyl alcohol, n-octyl alcohol, dodecanol, stearyl alcohol, an alcohol of ethylene oxide adduct of oleyl alcohol, polyethylene glycol, trimethylolethane, trimethylolpropane, an alcohol of ethylene oxide adduct of ethylene urea, tris(2-hydroxyethyl) isocyanurate, pentaerythritol, dipentaerythritol, etc. It is preferable to use an alcohol having 4 or more carbon atoms.

Since the by-produced methanol is removed by azeotropic distillation together with methyl methacrylate, it is preferable to use methyl methacrylate in an excess amount as to the alcohol. That is, it is preferable to use methyl methacrylate/alcohol in a molar ratio of 2/1 or more, more preferably 2.5/1 to 5/1. When the amount of methyl methacrylate is too small, the reaction rate is lowered undesirably, whereas when the amount is too large, there is no special advantage and rather there is a tendency to be less advantageous economically.

Lithium hydroxide, which is used as a catalyst, is preferably used in an anhydrous form or as dried form obtained by drying monohydrate thereof. Lithium hydroxide is preferably used in an amount of 0.1 to 5.0% by weight based on the weight of the alcohol.

When lithium hydroxide monohydrate is used as it is, it is necessary to take it into consideration that 18 g of water is contained in 42 g of lithium hydroxide monohydrate. For example, when lithium hydroxide monohydrate is added in an amount of 0.5% by weight to a mixture of 3 moles of methyl methacrylate and 1 mole of an alcohol, the water content becomes about 840 ppm only by the water of crystallization. Thus, even if the water content of the mixture of alcohol and methyl methacrylate is less 1000 ppm, the addition of the water of crystallization of lithium hydroxide to such a water content makes the resulting water content more than 1000 ppm, which results in difficult to obtain the effect of the present invention.

It is preferable to use a polymerization inhibitor which can inhibit by-reactions such as polymerization due to vinyl groups of the methyl methacrylate during the reaction and methacrylic acid produced. Examples of the polymerization inhibitor are hydroquinone, hydroquinone monomethyl ether, phenothiazine, catechol, etc. These polymerization inhibitors can be used alone or as a mixture thereof in an amount of preferably 10 to 1000 ppm.

The transesterification reaction can be carried out at 80° to 120° C. for 2 to 20 hours.

In the present invention wherein esterification is carried out by transesterification reaction of an alcohol and methyl methacrylate using lithium hydroxide as a catalyst, the water content of the three components of lithium hydroxide, alcohol and methyl methacrylate should be 1000 ppm or less. The water content can be measured by a known method, preferably by Karl Fischer's method from the viewpoint of easiness.

In the transesterification reaction, since methyl methacrylate is always reacted while refluxing, the water in the reactor is inherently distilled azeotropically together with methyl methacrylate and thus can be removed easily. But when the total water content of alcohol and methyl methacrylate is more than 1000 ppm, the removal of water by azeotropic distillation together with methyl methacrylate cannot be carried out rapidly, so that the co-existence time of the catalyst and water becomes long. As a result, a large amount of lithium salt of methacrylic acid is produced, although the mechanism of the formation is not clearly known, and the filtration time at the removal of catalyst is undesirably prolonged.

Thus, when commercially available alcohols and methyl methacrylate are used as they are and have a total water content of more than 1000 ppm, a polymerization inhibitor is first added to a mixture of the alcohol and methyl methacrylate, followed by removal of water by distillation with heating while refluxing to lower the water content to less than 1000 ppm. Then, the catalyst is added thereto to carry out the reaction. It is also possible to previously adjust the water contents of commercially available alcohols and methyl methacrylate properly, respectively, followed by the reaction.

After the reaction, unreacted methyl methacrylate is removed under reduced pressure with heating, followed by removal of the catalyst and the like by filtration. In this case, it is possible to use diatomaceous earth, for example, as a filter aid, in an amount of preferably 0.05 to 5.0% by weight based on the weight of the methacrylic acid ester. The filtration can be carried out by known method such as filtration by means of suction under reduced pressure, filtration under pressure, natural filtration under normal atmosphere, etc.

EXAMPLE 1

In a 3000-liter reactor equipped with a stirrer, a thermometer, an air introducing pipe, a distillation column and a reflux condenser, 776 kg (4 kmoles) of dicyclopentenyloxyethyl alcohol, and 1200 kg (12 kmoles) of methyl methacrylate were placed and mixed well with stirring. The water content of the resulting mixture was 800 ppm. The water content was measured by using a Karl Fischer type digital microamount water content measuring device (mfd. by Mitsubishi Chemical Industries Ltd.). Subsequently, 3 kg of anhydrous lithium hydroxide as a catalyst and 390 g of hydroquinone monomethyl ether as a polymerization inhibitor were added to the reactor, and the reaction was carried out while introducing dried air at a rate of 4 $m^3$/hr and refluxing the methyl methacrylate through the distillation column. While removing methanol by-produced by the reaction from the distillation column, the reaction was continued until almost no methanol was distilled (about 8 hours), followed by removal of unreacted methyl methacrylate under reduced pressure. After cooling, the reaction solution was filtered under pressure (5 kg/$cm^2$) using a filter paper (pore size 0.1 mm, area 5 $m^2$) placing thereon 10 kg of diatomaceous earth to yield 943 kg of dicyclopentenyloxyethyl methacrylate. The filtering time was 2.5 hours.

COMPARATIVE EXAMPLE 1

The process of Example 1 was repeated except that the total water content of dicycloentenyloxyethyl alcohol and methyl methacrylate was 1500 ppm. Dicyclopentenyloxyethyl methacrylate was obtained in yield of 965 kg with the filtrating time of 4 hours 45 minutes.

EXAMPLE 2

In the same reactor as used in Example 1, 760 kg (5 kmoles) of tricyclo[$5.2.1.0^{2,6}$]deca-8-yl alcohol and 1500 kg (15 kmole) of methyl methacrylate were placed and well mixed with stirring. The water content of the resulting mixture was 2500 ppm. To the mixture, 550 g of hydroquinone monomethyl ether was added and heated while introducing thereinto dried air at a rate of 4 $m^3$/hr and reluxing methyl methacrylate through the distillation column to remove water by azeotropic distillation. After 1 hour from the beginning of the reflux of methyl methacrylate, the water content in the reactor became 630 ppm. Then, 3 kg of anhydrous lithium hydroxide was charged into the reactor to carry out the reaction. While removing methanol by-produced by the reaction from the reaction system by distillation, the reaction was continued until almost no methanol was distilled (about 7 hours), followed by removal of unreacted methyl methacrylate under reduced pressure. After cooling, the mixture was filtered under pressure (2 kg/$cm^2$) using a filter paper (pore size 0.1 mm, area 5 $m^2$) placing thereon 10 kg of diatomaceous earth to yield 990 kg of tricyclo[$5.2.1.0^{2,6}$]deca-8-yl methacrylate with the filtrating time of 2 hours.

COMPARATIVE EXAMPLE 2

In the same reactor as used in Example 1, 760 kg (5 kmoles) of tricyclo[$5.2.1.0^{2,6}$]deca-8-yl alcohol and 1500 kg (15 kmoles) of methyl methacrylate were placed and well mixed with stirring. The water content of the mixture was 2500 ppm. To the mixture, 550 g of hydroquinone monomethyl ether and 3 kg of anhydrous lithium hydroxide were added to carry out the reaction. While refluxing methyl methacrylate through the distillation column, by-produced methanol was removed by distillation. The reaction was continued until almost no methanol was produced (about 7 hours). After removing unreacted methyl methacrylate by distillation under reduced pressure, the reaction mixture was cooled and filtered under pressure (2 kg/$cm^2$) using a filter paper (pore size 0.1 mm, area 5 $m^2$) placing thereon 10 kg of diatomaceous earth to yield 975 kg of tricyclo[$5.2.1.0^{2,6}$]deca-8-yl methacrylate with the filtrating time of 5.5 hours.

As mentioned above, according to the present invention, the time required for removing the catalyst and the like by filtration after the reaction can be shortened remarkably.

In the present invention wherein an alcohol and methyl methacrylate are subjected to the transesterification reaction in the presence of a catalyst and a polymerization inhibitor, while adding the same alcohol used as a starting material to the reaction system at a stage when the alcohol initially added is converted to 40% or more, or a later stage thereafter, the following conditions are employed.

Methyl methacrylate is used in an amount of preferably 1.5 to 10 moles, more preferably 2.5 to 5 moles, per mole of the starting alcohol.

As the alcohol, there can be used, for example, tricyclo[5.2.1.0$^{2,6}$]decenol, tricyclo[5.2.1.0$^{2,6}$]decanol, tricyclo[5.2.1.0$^{2,6}$]decenyloxyethanol, tricyclo[5.2.1.0$^{2,6}$]decanyloxyethanol, tricyclo[5.2.1.0$^{2,6}$]decenyloxypropanol, tricyclo[5.2.1.0$^{2,6}$]decanyloxypropanol, tricyclo[5.2.1.0$^{2,6}$]decenyloxyethanol, tricyclo[5.2.1.0$^{2,6}$]decanyloxyethoxyethanol, cyclohexanol, cyclooctanol, cyclododecanol, borneol, phenetol, cyclopentanol, ethyl alcohol, propyl alcohol, butyl alcohol, pentyl alcohol, hexyl alcohol, 2-ethylhexyl alcohol, n-octyl alcohol, dodecanol, stearyl alcohol, an alcohol of ethylene oxide adduct of oleyl alcohol, polyethylene glycol, trimethylolethane, trimethylolpropane, an alcohol of ethylene oxide adduct of ethylene urea, tris(2-hydroxyethyl) isocyanurate, pentaerythritol, dipentaerythritol, etc.

It is preferable to use an alcohol having 4 or more carbon atoms.

It is preferable to use a polymerization inhibitor which can inhibit side reactions such as polymerization due to vinyl groups of the methyl methacrylate and the produced methacrylic acid ester during the reaction. Examples of the polymerization inhibitor are hydroquinone, hydroquinone monomethyl ether, phenothiazine, catechol, etc. These polymerization inhibitors can be used alone or as a mixture thereof in an amount of preferably 10 to 10000 ppm.

As a catalyst for the transesterification reaction, it is preferable to use a titanium alkoxide, lithium hydroxide, etc. It is preferable to use the catalyst in an amount of 0.1 to 5% by weight based on the weight of the reactants.

It is also preferable to initially charge the reaction liquid in an amount of 45 to 60% by volume of the total volume of the reactor. When the initial charging volume is too much, there undesirably takes place a flooding phenomenon in a rectifying column due to bubbling from the reactor during the reaction. On the other hand, when the initial charging volume is too small, there is no special advantage and rather there is a tendency to make the reaction operation complicated.

The transesterification reaction is usually carried out under a normal pressure. From the viewpoint of preventing polymerization, the reaction is often carried out under a reduced pressure of preferably 200 to 760 Torr at a lower temperature. In order to carry out the transesterification reaction economically, the following points are important.

(1) In order to increase the reaction rate of transesterification reaction which is an equilibrium reaction, the vaporizing amount from the reactor is maintained at a predetermined amount so as to reduce the methanol concentration in the reactor.

(2) In order to make the composition of a mixture of methanol and methyl methacrylate distilled from the rectifying column near the azeotropic composition, the reflux ratio in the rectifying column is maintained at a predetermined value.

When the reflux ratio of rectifying column is increased, the methanol concentration in a reflux liquid is increased, which sometimes results in increasing the methanol concentration in the reactor. Thus, both are fundamentally contradictory.

Thus, in order to reconcile both operations, certain conditions are required for the reactor and the rectifying column. These conditions are changed depending on the kind of starting alcohol used and reaction conditions and cannot be determined evenly. But once the kind of starting alcohol and reaction conditions are determined and kinetic data such as reaction rates and equilibrium constant, and fundamental physical data such as vapor pressures of individual components, gasliquid equilibrium, etc, are provided, it is not a difficult thing to design an apparatus which can reconcile the two operations applying technical knowledge in this art.

When the transesterification reaction is carried out by satisfying the above-mentioned conditions, the vaporizing rate from the reactor becomes larger with vigorous bubbling. Particularly when the reaction is carried out under reduced pressure, since the vaporizing rate increases in inverse proportion to the pressure, the bubbling is remarkable. In such a case, even if the charging amount is made as small as 45 to 60% of the reactor volume, the bubbling surface reaches an upper end portion of the reactor at the initial stage of the reaction. Therefore, 60% is the limit of the charging amount.

The present inventors observed in detail the state of bubbling in the reactor during the reaction and found that the bubbling decreases with the progress of the reaction and when the conversion of the starting alcohol initially charged becomes 40% or more, the bubbling height decreases to form a space portion in the reactor.

In the present invention, the same alcohol as used as the starting alcohol is newly added when the conversion of the initially charged alcohol becomes 40% or more. The addition may be conducted at any time after the conversion reaches 40%. From the viewpoint of making the completion of the reaction fast, it is preferable to conduct the addition before the conversion of 80%.

When there takes place a trouble such as a lowering of the reaction rate or polymerization due to the reaction temperature rise, methyl methacrylate can be added to the reaction system simultaneously or after the addition of the alcohol. In this case, it is preferable to add a mixture of starting alcohol and methyl methacrylate in an amount so as to make the volume of the reaction solution after the addition 65 to 80% by volume based on the volume of the reactor. When the volume is less than 65% by volume, there is no effect for improving the productivity, while when the volume is more than 80% by volume, the reaction is undesirably easily influenced by outer factors such as variation in reaction conditions, and the like.

By adding in the range mentioned above, the bubbling height is not increased, even if the amount of reaction solution is increased, which results in making it possible to carry out the reaction stably. Since the latent heat and boiling point of the reaction solution are changed by the addition of alcohol, it is important to set the flowing amount for the addition and heating amount properly considering the heat balance in the reactor and the rectifying column so as to maintain the predetermined vaporizing amount and the reflux ratio. By conducting the reaction in such a manner, the producing amount of methacrylic acid ester can be increased to improve the productivity per batch without worsening the reaction rate and the composition of methanol and methyl methacrylate distilled from the rectifying column.

EXAMPLE 3

In a 7000-liter stirring-type reactor (total volume 7800 liters) equipped with a stirrer, a thermometer, an air introducing pipe and a rectifying column (a perforated tray tower, a diameter of tower 750 mm, 15 steps), 1700 kg (1589 liters) of ethylene glycol monodicyclopentenyl ether (EGD) of the formula:

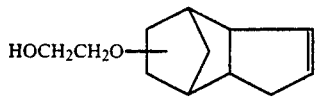

and 3.4 kg of dried lithium were placed. Subsequently, 2300 kg (2439 liters) of methyl methacrylate and 0.55 kg of phenothiazine were charged thereto with stirring. The charged volume was about 52% based on the reactor volume. The height of the charged liquid was 1350 mm in terms of the distance from the straight wall beginning portion at the bottom of the reactor (hereinafter referred to as "Liquid height").

The pressure inside of the reactor was reduced (the top pressure of rectifying column 320 Torr) and dried air was introduced into the reaction solution at a rate of 4 m³/hr, while passing steam through a reactor jacket at a rate of 400 kg/hr to increase the temperature. When the reaction solution temperature became near 60° C., vaporization began to distill off a mixture of methanol and methyl methacrylate from the top of rectifying column. After about 15 minutes' full reflux, the reflux ratio was made 3 and the reaction was continued while removing a part of distilled liquid out of the system. The conversion of starting alcohol was 32% at the beginning of full reflux. The liquid height including bubbles was 2400 mm and increased near the upper end portion of the reactor, but the rectifying column functioned normally without producing an abnormal phenomenon such as flooding. After about 15 minutes from the end of full reflux, the conversion of starting alcohol reached 50% and the liquid height including bubbles was reduced to 2050 mm, so that 500 kg of EGD was newly added at a flow rate of 1 m³/hr. During the addition of EGD, the liquid height including bubbles was gradually reduced to 2000 mm at the end of the addition of EGD to form about 27% by volume of a space in the reactor.

After 15 minutes from the end of the addition of EGD, 670 kg of methyl methacrylate (MMA) was added to the reaction-system at a flow rate of 1.2 m³/hr. When the addition of MMA was ended, the liquid volume in the reactor became about 67%. During the addition of methyl methacrylate, since the boiling point of the reaction solution was lowered, the flow rate of steam was reduced to 350 kg/hr. At this time, although the practical flow rate was increased, the liquid height including bubbles was lowered to 1900 mm after the addition of methyl methacrylate.

During such an operation, the reflux ratio of rectifying column was increased from 3 to 10 and the top temperature of rectifying column was maintained at about 44° C. The reaction was further continued and the reflux ratio was raised to 20 at the latter half of the reaction and the reaction was ended when the conversion of alcohol reached 99.5%. The reaction time was 220 minutes after the beginning of temperature rise.

Then, methyl methacrylate retained in the reaction solution was removed by distillation under reduced pressure. After cooling to room temperature, the catalyst and the like were removed by filtration to give 2910 kg of methacrylic acid ester of ethylene glycol monodicyclopentenyl ether (EGD-MA) of the formula:

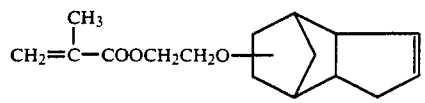

in yield of 98%.

The composition of a mixture of methanol and methyl methacrylate distilled from the rectifying column during the reaction was near the azeotropic composition and contained methanol in 88 mole %.

COMPARATIVE EXAMPLE 3

The process of Example 3 was repeated except for not newly adding 500 kg of EGD and 670 kg of methyl methacrylate when the conversion of alcohol reached 50% to give EGD-MA in an amount of 2240 kg (yield 98%).

The productivity per batch was reduced by 670 kg compared with Example 3.

COMPARATIVE EXAMPLE 4

In the same apparatus as used in Example 3, 200 kg (2075 liters) of EGD and 3.4 kg of dried lithium hydroxide were charged. Subsequently, 2970 kg (3150 liters) of methyl methacrylate and 0.55 kg of phenothiazine were charged thereto with stirring. The volume of charged liquid was about 67% based on the volume of the reactor. The pressure inside of the reactor was reduced (the top pressure of rectifying column 320 Torr) and dried air was introduced into the reaction solution at a rate of 4 m³/hr, while passing steam through a reactor jacket at a rate of 400 kg/hr to increase the temperature. When the reaction solution temperature became near 60° C., vaporization began. After about 5 minutes from the beginning of vaporization, bubbles went over the upper portion of the reactor and raised to the rectifying column tower through a vapor leading pipe, while causing a flooding phenomenon. Then, the reaction solution was blown off from the top of rectifying column. Thus, the reaction was forced to be stopped.

According to the process of the present invention, since the flooding phenomenon in the rectifying column due to bubbling during the reaction can be prevented, the charging amount can be 60% or more of the capacity of the reactor and thus the desired methacrylic acid ester can be produced with excellent productivity by making the producing amount per batch remarkably large.

In the present invention wherein an alcohol and methyl methacrylate are subjected to the transesterification reaction in the presence of a catalyst and a polymerization inhibitor, said catalyst being obtained by drying lithium hydroxide monohydrate with heating, the following conditions are employed.

In the case of drying lithium hydroxide monohydrate with heating, it is preferable to heat lithium hydroxide monohydrate at a temperature of 100° to 200° C. for 2 to 20 hours in the air. When the drying is carried out at a temperature lower than 100° C. for less than 2 hours, a sufficient effect cannot always be obtained, whereas when the drying is carried out at a temperature higher than 200° C. for more than 20 hours, there is no particular advantage.

The drying of lithium hydroxide monohydrate can be carried out by using a heating apparatus conventionally used such as a constant temperature chamber, a constant temperature tank, a hot-air drier, an oven, or the like. The drying operation can be carried out in vacuum, or by parging together with a $N_2$ gas using an apparatus suitable for such an operation.

The drying with heating can easily be carried out, for example, by placing lithium hydroxide monohydrate on a tray or dish made from a metal or glass and putting the tray or dish in a hot-air drier. By drying in this way, the weight of lithium hydroxide monohydrate is reduced in about 40 to 43% by weight. The thus dried lithium hydroxide can be used as a catalyst for the transesterification reaction. In the case of storing the catalyst for a long period of time, it is preferable to store the dried lithium hydroxide in a can, bottle, bag made from a polyvinyl chloride, plastic container, or the like.

As the alcohol used as a starting material, there can be used monohydric alcohols, e.g. saturated aliphatic alcohols such as ethanol, n-propanol, iso-propanol, n-butanol, iso-butanol, tert-butanol, n-pentanol, n-hexanol, n-heptanol, n-octanol, 2-ethyl-hexanol, lauryl alcohol, cetyl alcohol, steary alcohol, etc.; unsaturated aliphatic alcohols such as allyl alcohol, oreyl alcohol, etc.; saturated or unsaturated alicyclic alcohols (including compounds having an ether bond) such as cyclopentanol, cyclohexanol, cyclooctanol, cyclododecanol, bicyclo[2.2.1]hept-2-en-5-ol, bicyclo[2.2.1]heptan-2-ol, cyclohexanemonomethylol, bicyclo[2.2.1]hept-2-en-5-yl-methanol, bicyclo[2.2.1]heptan-2-yl-methanol, 1-adamantol, 2-adamantol, tricyclo[5.2.1.0$^{2,6}$]deca-3-en-8(or 9)-ol, tricyclo[5.2.1.0$^{2,6}$]decan-8-ol, tricyclo[5.2.1.0$^{2,6}$]decan-3(or 4)-yl-methanol, borneol, isoborneol, fenchyl alcohol, 2,2,5-trimethylcyclohexanol, menthol, ethylene glycol monodicyclopentenyl ether, propylene glycol monodicyclopentenyl ether, neopentyl glycol monodicyclopentenyl ether, 1,6-hexanediol monodicyclopentenyl ether, etc.; alkylamino alcohols such as dimethylamino ethanol, diethylamino ethanol, etc.; alcohols having a heterocyclic ring structure such as tetrahydrofurfuryl alcohol, N-hydroxyethylmorpholine, 1,2,2,6,6-penta-methyl-4-piperidinol, 2,2,6,6-tetramethyl-4-piperidinol, alcohol of ethylene oxide adduct of ethylene urea, etc.; alcohols having an aromatic structure such as benzyl alcohol, phenetyl alcohol, cumyl alcohol, etc.; ether alcohols obtained by condensing an alcohol mentioned above, methanol and a phenol such as phenol, an alkylphenol and a dihydric alcohol. As the dihydric alcohol used for constituting the ether alcohols, there can be used ethylene glycol, 1,2-glycol, polyethylene glycol [HO—(CH$_2$CH$_2$O—)$_n$ H, n=2 or more],

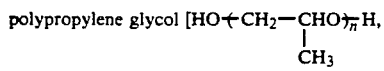

n=2 or more], etc. For example, an ether alcohol can preferably be obtained by addition of ethylene oxide or propylene oxide to an alcohol mentioned above, methanol and a phenol.

It is also possible to use dihydric or higher polyhydric alcohols such as ethylene glycol, propylene glycol, 1,4-butanediol, 1,3-butanediol, 1,6-hexanediol, neopentyl glycol, polyethylene glycol [HO—(CH$_2$CH$_2$O—)$_n$ H, n=2 ore more],

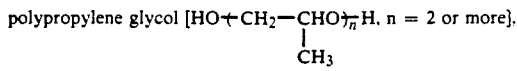

trimethylol propane, glycerin, tris(2-hydroxyethyl) isocyanurate, pentaerythritol, cyclohexane dimethylol, dicyclopentadiene dimethylol, and hydrogenated bisphenoil A; polyhydric ether alcohols obtained by addition polymerization of ethylene oxide or propylene oxide with a polyhydric alcohol as mentioned above, and a polyhydric phenol such as bisphenol A, bisphenol S, bis(p-hydroxylphenol) ether, bisphenol, etc.

As the catalyst for synthesizing a methacrylic acid ester by the transesterification reaction of such an alcohol as mentioned above and methyl methacrylate, when the compound obtained by drying lithium hydroxide monohydrate with heating (hereinafter referred to as "dried lithium hydroxide") as mentioned above is used, good catalytic activity is shown and separation of the catalyst from the reaction mixture after the reaction is remarkably easy.

In the case of using a secondary or tertiary alcohol as an alcohol, the reaction hardly proceeded when lithium hydroxide hydrate was used as a catalyst. In contrast, when the dried lithium hydroxide is used, the reaction is carried out smoothly, even if a secondary or tertiary alcohol is used.

In order to carry out the transesterification reaction, the dried lithium hydroxide is preferably used in an amount of 0.01 to 10.0% by weight, more preferably 0.05 to 5.0% by weight, based on the weight of the starting alcohol. When the amount is too small, the transesterification reaction proceeds too slow and sometimes the reaction is stopped during the reaction. On the other hand, when the amount is too much, the removal of the catalyst after the reaction becomes complicated.

In the transesterification reaction, methyl methacrylate is preferably used in an amount of 2 to 15 moles per equivalent weight of hydroxyl group of the starting alcohol. When the amount of methyl methacrylate is too small, the reaction becomes slow to easily retain unreacted starting alcohol. On the other hand, when the amount of methyl methacrylate is too much, the productivity becomes poor and a long time is necessary to recover excess methyl methacrylate after the reaction.

In the present invention, it is preferable to carry out the transesterification reaction in the presence of a polymerization inhibitor. As the polymerization inhibitor, there can be used conventional ones such as hydroquinone, hydroquinone monomethyl ether, t-butyl catechol, p-benzoquinone, 2,5-diphenyl p-benzoquinone, phenothizine, diphenylamine, phenol-β-naphthylamine, methylene blue, etc. The polymerization inhibitor is preferably used in an amount of 15 to 10,000 ppm, more preferably 50 to 1000 ppm based on the weight of the starting alcohol. When the amount is too small, the effect for inhibiting polymerization becomes insufficient, whereas when the amount is too much, a product from which the polymerization inhibitor is not completely removed is provided for polymerization, which results in giving a bad influence such as inhibition of polymerization in the later polymerization process. The use of hydroquinone monomethyl ether or phenothiazine is preferable from the viewpoint of preventing coloring of the reaction solution.

Further, in order to prevent polymerization during the reaction, it is preferable to further introduce a small amount of molecular oxygen to the reaction solution. As the molecular oxygen, it is preferable to use it in a diluted form such as an air. The introduction of molecular oxygen is also effective for preventing polymerization of methyl methacrylate present as a gas or liquid in a rectifying tower in the case of using such a rectifying tower as mentioned below. The using amount of molecular oxygen changes depending on the shape of reactors, stirring power, and the like, and is preferably 2 to 500 ml/min (10 to 2500 ml/min converted to air) in terms of an introducing rate per mole of the starting alcohol.

It is preferable to introduce dry air or oxygen having a water content of preferably 1% by weight or less, more preferably 1000 ppm or less. The removal of water can be carried out, for example, by adsorbing water from compressed air using sulfuric acid, molecular sieve, calcium chloride, silica gel, etc., or condensing water by cooling. It is also possible to use purified liquid oxygen as it is or diluted with nitrogen or the like.

The reaction at an elevated temperature can be carried out after charging the whole amounts of the starting materials into a reactor. When an oxidizable alcohol such as an alicyclic alcohol or an alcohol containing an ether bond is used, it is advantageous to charge the alcohol and dried lithium hydroxide previously, and stirring well, followed by addition of a polymerization inhibitor and methyl methacrylate in order to prevent a trouble such as polymerization during the synthetic reaction.

The whole amount of the dried lithium hydroxide can be charged before the reaction, or a part of the catalyst can be added to the reaction system during the reaction dividedly.

The transesterification reaction can preferably be carried out at 60 to 130° C. under a normal pressure or reduced pressure.

As a reaction method of the transesterification reaction, there can be used any methods known to those skilled in the art for producing methacrylic acid esters by transesterification reactions of methyl methacrylate and an alcohol. In such a method, it is preferable to carry out the reaction while removing methanol by-produced out of the system by azeotropic distillation together with methyl methacrylate in order to increase the conversion of the starting alcohol.

As a reaction apparatus, it is preferable to use a batch type reactor attaching a rectifying tower. In this case, the transesterification reaction is carried out, for example, as follows. That is, in the case of carrying out the reaction under a normal pressure, when the reacting liquid temperature is raised to about 100° C., produced methanol and methyl methacrylate are boiled. By controlling a reflux ratio (in the range of about 1 to 20) so as to make the top portion temperature of the rectifying tower in the range of 64° C. to 70° C. which temperature is an azeotropic point of methanol and methyl methacrylate, the transesterification reaction is completed while removing methanol out of the system as an azeotrope together with methyl methacrylate and making the amount of methyl methacrylate distilled out of the system as small as possible. In this case, the reacting liquid temperature is raised to about 110 to 125° C. near the end point of the reaction, and the tower top temperature becomes about 100° C. That is, since the composition is varied from the azeotropic composition of methanol and methyl methacrylate, it is preferable to make the reflux ratio larger (10 or more) in order to lessen the loss of methyl methacrylate.

On the other hand, when methanol is retained in the reaction system in a high concentration for a long period of time, since a by-product obtained by adding methanol to the unsaturated bond of methacrylic acid ester is produced, it is necessary to remove the methanol produced out of the system as fast as possible by distillation in order to lessen the produced amount of methanol.

In the rectifying tower, there is a large amount of a liquid and a gas of methyl methacrylate evaporated from the reactor. But, even if a polymerization inhibitor is charged into the reactor, since it does not evaporate simply, almost no polymerization inhibitor is present in the rectifying tower. Thus, there is a fear of causing polymerization of methyl methacrylate therein. In such a case, it is preferable to introduce molecular oxygen (e.g. air) into the reactor and to make the molecular oxygen present in the rectifying tower, or to add a polymerization inhibitor to a reflux liquid returning to the rectifying tower from the tower top.

The reaction mixture obtained by the transesterification reaction comprises, in many cases, a solution of methyl methacrylate, the desired product of methacrylic acid ester, a small amount of the starting alcohol and a polymerization inhibitor and insoluble materials such as the catalyst, and the like.

In order to obtained the desired product by substantially isolating the produced methacrylic acid ester from the reaction mixture, the insoluble materials such as the catalyst is removed by filtration from the reaction mixture, followed by removal of methyl methacrylate by distillation, or alternatively methyl methacrylate is removed by distillation first, followed by removal of the insoluble materials such as the catalyst by filtration. Usually, the desired product can be obtained by such a procedure as mentioned above, and if necessary, may further be purified by distillation (usually distillation under reduced pressure).

In the case of filtering the reaction mixture after the reaction or the reaction mixture after removal of methyl methacrylate, it is possible to add about 0.1 to 2.0% by weight of a filter aid (usually diatomaceous earth) to the reaction mixture, or to precoat the filter aid on the surface of the filter. Any filtering methods such as a suction filtration under reduced pressure, a filtration under pressure, a natural filtration under a normal pressure, or the like can be employed.

According to Japanese Patent Unexamined Publication No. 54-61117, there is the following description:

"Lithium hydroxide is usually present in the form of dissolved state at the beginning of the transesterification reaction. In many cases, the lithium hydroxide is deposited from the reaction mixture with the progress of the reaction. But this does not damage the catalytic action at all."

The present inventors have studied this in detail and found that the lithium hydroxide was almost insoluble at the beginning of the reaction, and only a very small amount of lithium hydroxide was dissolved in the reaction solution to show a catalytic activity, and with the progress of the reaction the deposited thing was not the lithium hydroxide but a lithium salt of methacrylic acid, which had no catalytic activity and remarkably lowered filtering properties at the time of filtering the reaction mixture after the reaction. The present inventors have studied how to reduce the produced amount of lithium salt of methacrylic acid and found that the most effective thing is to use lithium hydroxide subjected to drying treatment with heating.

Further, in the case of using a secondary or tertiary alcohol, the use of lithium hydroxide hydrate seems to cause a trouble of mutual actions of the starting alcohol and lithium hydroxide.

EXAMPLE 4

(1) Drying of lithium hydroxide

In a tray made of stainless steel with a size of 50 cm wide, 70 cm long and 8 cm deep, 6.0 kg of particles of lithium hydroxide monohydrate were placed. The tray was put in a hot-air dryer heated at 150° C. for 5 hours for drying. After drying, the resulting dried lithium hydroxide weighted 3.4 kg.

(2) Synthesis of methacrylic acid ester

In a 3000-liter reactor equipped with a stirrer, a thermometer, an air introducing pipe and a rectifying column (connected to a condenser and a reflux device), 776 kg (4 kmoles) of dicyclopentenyloxyethyl alcohol of the formula:

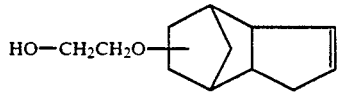

and 2.0 kg of the dried lithium hydroxide obtained in above (1) were placed. Subsequently, 390 g of hydroquinone monomethyl ether and 1200 kg (12 kmoles) of methyl methacrylate were added thereto with stirring, followed by introduction of a dried air into the reaction liquid at a rate of 2 m³/hr and a temperature rise to carry out the reaction under a normal pressure. After 1 hour from the beginning of the temperature rise, 0.5 kg of dried lithium hydroxide was added to the reaction system additionally. The reaction was carried out while removing methanol by-produced by the reactor from the top of the rectifying column as an azeotropic mixture with methyl methacrylate. The rectifying column top temperature was maintained at about 65° C. by adjusting the reflux ratio during the reaction. The column top temperature was raised near the end of the reaction and finally raised to about 100° C. During this time, the temperature of the reaction mixture was 100 to 115° C. After 6 hours' reaction, the amount of dicyclopentenyloxyethyl alcohol used as a starting alcohol became 0.4% by weight (calculated from the areas of gas chromatogram in percentage) based on the total of the alcohol and the desired product of methacrylic acid ester, and the reaction was finished.

Then, the temperature of the reaction mixture was made 100° C. and the methyl methacrylate was distilled out by gradually reducing the pressure to 40 mmHg finally. The concentration was stopped when the methyl methacrylate content became 0.15% by weight measured by gas chromatography.

After cooling the concentrated solution to room temperature, filtration was carried out under pressure (3 kg/cm²) using a pressure filtering device with a filter paper (pore size 0.1 mm, area 5 m²) precoated with 10 kg of diatomaceous earth to give 985 g (yield 94%) of dicyclopentenyloxyethyl methacrylate of the formula:

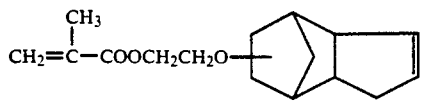

The time required for the filtration was 1 hour 50 minutes.

COMPARATIVE EXAMPLE 5

The reaction was carried out in the same manner as described in Example 4 except for using 3.0 kg of lithium hydroxide monohydrate in place of 2.0 kg of the dried lithium hydroxide used in Example 4 and 0.8 kg of additional lithium hydroxide monohydrate in place of 0.5 kg of the additional lithium hydroxide used in Example 4. When the reaction time became 7 hours, the amount of the starting dicyclopentenyloxyethanol became 0.9% by weight (calculated from the areas of gas chromatogram in percentage) based on the total of the alcohol and the desired product of methacrylic acid ester.

After the reaction, the methyl methacrylate was removed by distillation and the filtration was conducted in the same manner as described in Example 4. As a result, dicyclopentenyloxyethyl methacrylate was obtained in an amount of 935 kg (yield 89%). The time required for the filtration was 5 hours 20 minutes.

EXAMPLE 5

(1) Drying of lithium hydroxide

In a tray made of stainless steel with a size of 50 cm wide, 70 cm long and 8 cm deep, 7.0 kg of particles of lithium hydroxide monohydrate were placed. The tray was put in a hot-air dryer heated at 120° C. for 10 hours for drying. After drying, the resulting dried lithium hydroxide weighed 4.05 kg.

(2) Synthesis of methacrylic acid ester

In the same 3000-liter reactor as used in Example 4, 760 kg (5 moles) of 8-tricyclo[5.2.1.0$^{2,6}$]decanol and 3.0 kg of the dried lithium hydroxide were placed. Subsequently 550 g of hydroquinone monomethyl ether and 1500 kg (15 kmoles) of methyl methacrylate were added thereto with stirring, followed by introduction of an air into the reaction liquid at a rate of 2 m³/hr and a temperature rise to carry out the reaction under a normal pressure. The reaction was carried out while removing methanol by-produced by the reaction from the top of the rectifying column as an azeotropic mixture with methyl methacrylate and maintaining the rectifying column top temperature at about 65° C. by adjusting the reflux ratio properly. The column top temperature was raised near the end of the reaction and finally raised to about 100° C. During this time, the temperature of the reaction mixture was 103 to 118° C. After 7 hours' reaction, 8-tricyclo[5.2.1.0$^{2,6}$]decanol used as a starting alcohol became 0.3% by weight (calculated from the areas of gas chromatogram in percentage) based on the total of the alcohol and the desired product of methacrylic acid ester, and the reaction was finished.

Then, the temperature of the reaction mixture was made 100° C. and the methyl methacrylate was distilled out by gradually reducing the pressure to 40 mmHg finally. The concentration was stopped when the methyl methacrylate content became 0.15% by weight measured by gas chromatography.

After cooling the concentrated solution to room temperature, filtration was carried out under pressure (3 kg/cm²) using a pressure filtering device with a filter paper (pore size 0.1 mm, area 5 m²) precoated with 5 kg of diatomaceous earth to give 1040 kg (yield 94.5%) of tricyclo[5.2.1.0²,⁶]deca-8-yl methacrylate.

The time required for the filtration was 1 hour 35 minutes.

COMPARATIVE EXAMPLE 6

The reaction was carried out in the same manner as described in Example 5 except for using 5.0 kg of lithium hydroxide monohydrate in place of 3.0 kg of the dried lithium hydroxide used in Example 5. Even when the reaction time became 10 hours, the amount of the starting 8-tricyclo[5.2.1.0²,⁶]decanol was still 43% by weight based on the total of the alcohol and the desired product of methacrylic acid ester. Although the reaction was on route, methyl methacrylate was removed by distillation in the same manner as described in Example 5. The mixture containing 8-tricyclo[5.2.1.0²,⁶]decanol and tricyclo[5.2.1.0²,⁶]deca-8-yl methacrylate was filtered in the same manner as described in Example 5. The filtrate was in an amount of 810 kg and the time required for the filtration was 7 hours 30 minutes.

EXAMPLE 6

(1) Drying of lithium hydroxide

In a tray made of stainless steel with a size of 50 cm wide, 70 cm long and 8 cm deep, 8.0 kg of particles of lithium hydroxide monohydrate were placed. The tray was put in a hot-air dryer heated at 180° C. for 3 hours for drying. After drying, the resulting dried lithium hydroxide weighed 4.6 kg.

(2) Synthesis of methacrylic acid ester

In a 1-liter four-necked flask equipped with a stirrer, a thermometer, an air introducing pipe and a rectifying column, 150 g (1.5 moles) of cyclohexanol of the formula:

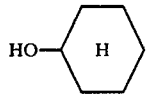

and 1.0 g of the dried lithium hydroxide were placed. Subsequently, 0.13 g of phenothiazine and 450 g of methyl methacrylate were added thereto with stirring, followed by introduced of air at a rate of 100 ml/min and a temperature rise to carry out the reaction. The reaction was continued while adjusting the reflux ratio so as to make the rectifying column top temperature about 65° C.

The column top temperature was raised near the end of the reaction and finally raised to about 100° C. During this time, the temperature of the reaction mixture was 101° C. to 110° C. After 4 hours' reaction, the amount of cyclohexanol used as a starting alcohol became 0.3% by weight (calculated from the areas of gas chromatogram in percentage) based on the total of the alcohol and the desired product of methacrylic acid ester, and the reaction was finished.

The reaction mixture was subjected to distillation under reduced pressure to remove the methyl methacrylate, followed by cooling to room temperature. Then, the reaction mixture was subjected to suction filtration using a Buchner funnel with a filtering area of 70 cm² and using an aspirator. As a result, 225 g of cyclohexyl methacrylate was yielded. The time required for the filtration was 2 minutes 40 seconds.

COMPARATIVE EXAMPLE 7

The reaction was carried out in the same manner as described in Example 6 except for using 2.0 g of lithium hydroxide monohydrate in place of 1.0 g of the dried lithium hydroxide. Even after 10 hours' reaction, 12% by weight of cyclohexanol based on the total weight of cyclohexanol and cyclohexyl methacrylate was retained. The methyl methacrylate was removed by distillation under reduced pressure, followed by filtration in the same manner as described in Example 6.

The time required for the filtration was 56 minutes and the filtrate was 190 g.

According to the present invention, the removal of the catalysts by filtration after the reaction can easily be conducted.

Needless to say, the above-mentioned effects, that is, shortening of the filtration time of the catalyst and the like, prevention of generation of large bubbles during the reaction, and use of a secondary or tertiary alcohol as a starting material with high catalytic activity as well as easy filtration of the catalyst after the reaction, can be attained in combination, by combining the above-mentioned steps of conditions, two or more, respectively.

EXAMPLE 7

The process of Example 3 was repeated while making the total water content in the catalyst, alcohol and methyl methacrylate 800 pm as in Example 1.

The same effects as obtained in Example 3 and Example 1 were obtained.

EXAMPLE 8

The process of Example 4 was repeated while making the total water content in the catalyst, alcohol and methyl methyacrylate 800 ppm as in Example 1.

The same effects as obtained in Example 4 and Example 1 were obtained.

EXAMPLE 9

The process of Example 4 was repeated while making the total water content in the catalyst, alcohol and methyl methacrylate 800 ppm as in Example 1 and adding 500 kg of EGD to the reaction system at a flow rate of 1 m³hr when the conversion of the starting alcohol reached 50% as in Example 3.

The same effects as obtained in Example 4, Example 1 and Example 3 were obtained.

What is claimed is:

1. A process for producing a methacrylic acid ester, which comprises subjecting an alcohol and methyl methacrylate to a transesterification reaction in the presence of a catalyst and a polymerization inhibitor, said catalyst being obtained by drying lithium hydroxide monohydrate with heating at 100° to 200° C. for 2 to 20 hours in air.

2. A process according to claim 1, wherein a total water content in the catalyst, alcohol and methyl methacrylate is 1000 ppm or less.

3. A process according to claim 2, wherein the catalyst is lithium hydroxide.

4. A process according to claim 3, wherein the lithium hydroxide is anhydrous one or that obtained by drying lithium hydroxide monohydrate.

5. A process according to claim 2, wherein the alcohol is selected from the group consisting of tricyclo[5.2.1.0$^{2,6}$]decenol, tricyclo[5.2.1.0$^{2,6}$]decanol, tricyclo[5.2.1.0$^{2,6}$]decenoloxyethanol, tricyclo[5.2.1.0$^{2,6}$]decanyloxyethanol, tricyclo[5.2.1.0$^{2,6}$]decenyloxypropanol, tricyclo[5.2.1.0$^{2,6}$]decanyloxypropanol, tricyclo[5.2.1.0$^{2,6}$]decenyloxyethanol, cyclohexanol, cyclooctanol, cyclododencanol, borneol, phenetol, cyclopentanol, ethyl alcohol, propyl alcohol, butyl alcohol, pentyl alcohol, hexyl alcohol, 2-ethylhexyl alcohol, n-octyl alcohol, dodecanol, stearyl alcohol, an alcohol of ethylene oxide adduct of oleyl alcohol, polyethylene glycol, trimethylolethane, trimethylolpropane, an alcohol of ethylene oxide adduct of ethylene urea, tris(2-hydroxyethyl) isocyanurate, pentaerythritol, and dipentaerythritol.

6. A process according to claim 1, wherein the transesterification reaction is carried out at a temperature of 80° C. to 120° C.

7. A process according to claim 1, which further comprises adding the same alcohol as used as a starting material to the reaction system at a stage when the alcohol initially added is converted to 40% or more, or a later stage thereafter.

8. A process according to claim 7, wherein the alcohol is selected from the group consisting of tricyclo[5.2.1.0$^{2,6}$]decenol, tricyclo[5.2.1.0$^{2,6}$]decanol, tricyclo[5.2.1.0$^{2,6}$]decenyloxyethanol, tricyclo[5.2.1.0$^{2,6}$]decanyloxyethanol, tricyclo[5.2.1.0$^{2,6}$]decenyloxypropanol, tricyclo[5.2.1.0$^{2,6}$]decanyloxypropanol, tricyclo[5.2.1.0$^{2,6}$]decenyloxyethanol, tricyclo[5.2.1.0$^{2,6}$]decanyloxyethoxyethanol, cyclohexanol, cyclooctanol, cyclododencanol, borneol, phenetol, cyclopentanol, ethyl alcohol, propyl alcohol, butyl alcohol, penty alcohol, hexyl alcohol, 2-ethylhexyl alcohol, n-octyl alcohol, dodecanol, stearyl alcohol, an alcohol of ethylene oxide adduct of oleyl alcohol, polyethylene glycol, trimethylolethane, trimethylolpropane, an alcohol of ethylene oxide adduct of ethylene urea, tris(2-hydroxyethyl) isocyanurate, pentaerythritol, and dipentaerythritol.

9. A process according to claim 7, wherein the alcohol is added in the form of a mixture of starting alcohol and methyl methacrylate in an amount so as to make the volume of the reaction solution after the addition 65 to 80% by volume based on the volume of the reactor.

10. A process according to claim 1, wherein the alcohol is a primary, secondary or tertiary alcohol.

11. A process according to claim 1, wherein the alcohol is a secondary or tertiary alcohol.

12. A process for producing a highly pure methacrylic acid ester, which comprises subjecting methyl methacrylate and an alcohol to a transesterification reaction in the presence of a catalyst and a polymerization inhibitor, while making a total water content in the catalyst, alcohol and methyl methacrylate being 1000 ppm or less, adding the same alcohol as used as a starting material to the reaction system at a stage when the alcohol initially added is converted to 40% or more, or a later stage thereafter, and using as the catalyst that obtained by drying lithium hydroxide monohydrate with heating at 100° to 200° C. for 2 to 20 hours in air.

13. A process according to claim 12, wherein the methyl methacrylate and the alcohol are in a molar ratio of 2/1 or more and the catalyst is used in an amount of 0.1 to 5.0% by weight based on the weight of the alcohol.

14. A process according to claim 13, wherein the polymerization inhibitor is hydroquinone, hydroquinone monomethyl ether, phenothiazine or catechol or a mixture thereof and the polymerization inhibitor is used in an amount of 10 to 1000 ppm.

15. A process according to claim 1, wherein the alcohol is selected from the group consisting of tricyclo[5.2.1.0$^{2,6}$]decenol, tricyclo[5.2.1.0$^{2,6}$]decanol, tricyclo[5.2.1.0$^{2,6}$]decenyloxyethanol, tricyclo[5.2.1.0$^{2,6}$]decanyloxyethanol, tricyclo[5.2.1.0$^{2,6}$]decenyloxypropanol, tricyclo[5.2.1.0$^{2,6}$]decanyloxypropanol, tricyclo[5.2.1.0$^{2,6}$]decenyloxyethanol, tricyclo[5.2.1.0$^{2,6}$]decanyloxyethoxyethanol, cyclohexanol, cyclooctanol, cyclododencanol, borneol, phenetol, cyclopentanol, ethyl alcohol, propyl alcohol, butyl alcohol, penty alcohol, hexyl alcohol, 2-ethylhexyl alcohol, n-octyl alcohol, dodecanol, stearyl alcohol, an alcohol of ethylene oxide adduct of oleyl alcohol, polyethylene glycol, trimethylolethane, trimethylolpropane, an alcohol of ethylene oxide adduct of ethylene urea, tris(2-hydroxyethyl) isocyanurate, pentaerythritol, and dipentaerythritol.

16. A process according to claim 1, wherein the transesterification reaction is carried out at a temperature of 80° to 120° C.

17. A process according to claim 1, wherein the methyl methacrylate and the alcohol are in a molar ratio of 2/1 or more and the catalyst is used in an amount of 0.1 to 5.0% by weight based on the weight of the alcohol.

18. A process according to claim 17, wherein the polymerization inhibitor is hydroquinone, hydroquinone monomethyl ether, phenothiazine or catechol or a mixture thereof and the polymerization inhibitor is used in an amount of 10 to 1000 ppm.

* * * * *